Oct. 12, 1971 R. V. LINDQUIST Plant Pat. 3,069
ROSE PLANT
Filed July 24, 1969
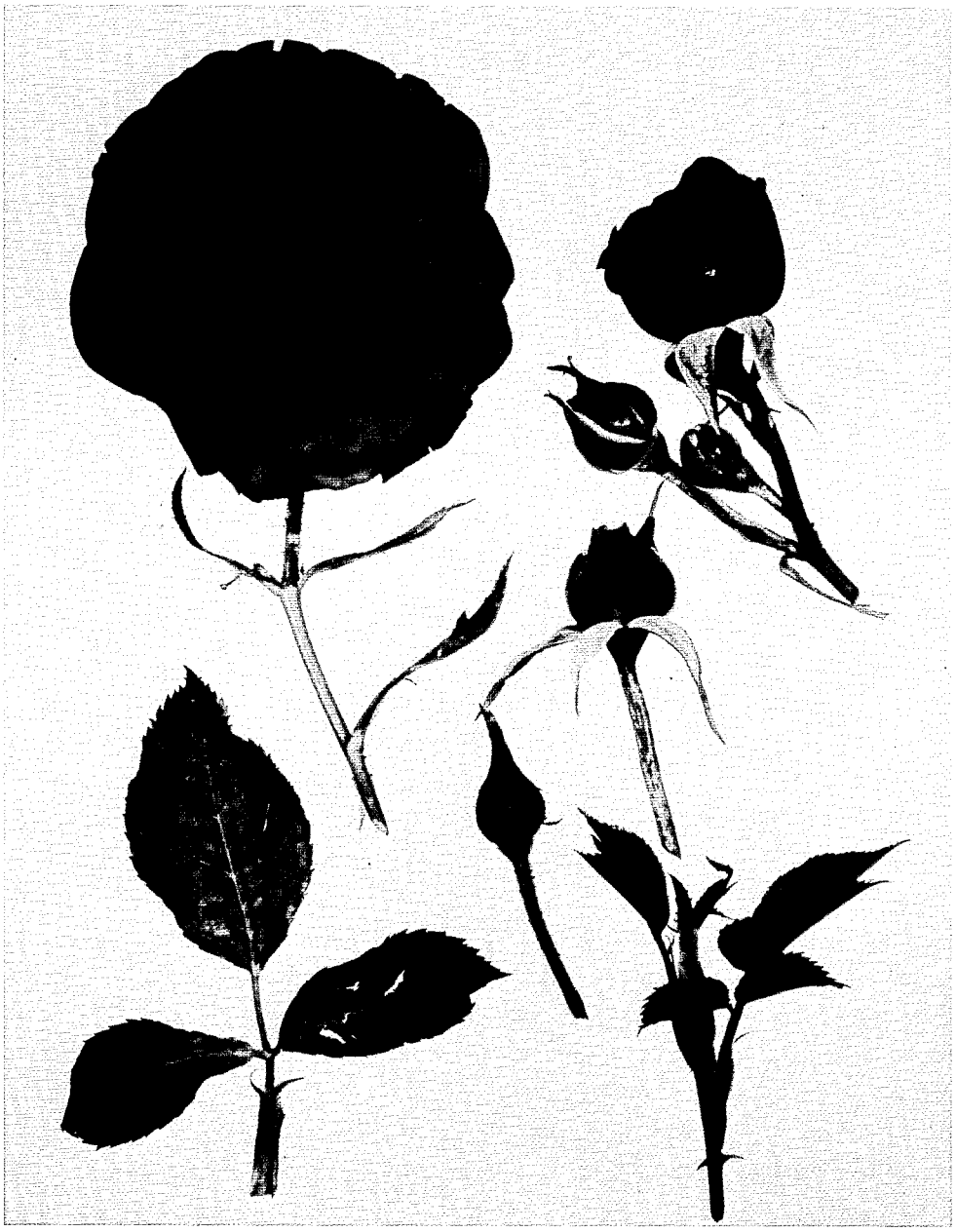
Inventor.
R. V. Lindquist
By: Robb & Robb
Attorneys.

United States Patent Office

Plant Pat. 3,069
Patented Oct. 12, 1971

3,069
ROSE PLANT

Robert V. Lindquist, Hemet, Calif., assignor to Hemet Wholesale, Hemet, Calif.

Filed July 24, 1969, Ser. No. 844,674
Int. Cl. A01h 5/00
U.S. Cl. Plt.—29 1 Claim The present invention relates to a new and distinct variety of rose plant of the floribunda class, which was originated by me by crossing the rose variety known as "Garnette" (unpatented) with the rose variety known as "Moulin Rouge" (Plant Patent No. 1,298), the former being the seed parent and the latter being the pollen parent.

As the result of this breeding, I have produced a new and improved rose variety which is distinguished from its parents, as well as from all other rose varieties of which I am aware, as evidenced by the following unique combination of characteristics which are outstanding in the new variety:

(1) A low-growing and vigorous plant habit;
(2) Excellent foliage;
(3) A free flowering habit;
(4) Dainty "Garnette"-like buds which open to small, flat, perfectly formed attractive full flowers of over 100 petals per flower on the average;
(5) A distinctive and attractive velvety red flower color;
(6) Good flower color retention even under adverse weather conditions; and
(7) An above average lasting quality of the flowers both on the bush and as cut flowers.

Asexual reproduction of my new variety by budding, as performed at Hemet, Calif., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new rose variety, with color terminology in accordance with the Royal Horticultural Colour Chart, published by the Royal Horticultural Society of London, except where general color terms of ordinary dictionary significance are obvious:

Type: Hardy; bush; outdoor; seedling; for cut flowers and for garden decoration.
Class: Floribunda.
Breeding: Seedling.
*Seed parent.*—"Garnette".
*Pollen parent.*—"Moulin Rouge."
Propagation: Holds its distinguishing characteristics through succeeding propagations by budding.

*Flower*

Locality where grown and observed: Hemet, California.
Flowers Borne: Usually several to stem; in irregular clusters; on strong stems of short to medium length.
Quantity of bloom: Very free, both outdoors and in greenhouse.
Continuity: Continuous during growing season.
Fragrance: Very slight.
*Nature.*—Musk.
Bud:
*Peduncle.*—From short to average length; average caliper; erect; moderately smooth; some gland-tipped cilia and few prickles. Color—Near Yellow-Green, Group 146 C.
*Before calyx breaks.*—

Size—Medium. Form—Short; globular; with a conspicuous neck; with foliaceous appendages and gland-tipped cilia on the surface of the bud; usually with slender, bristle-like foliaceous parts extending beyond the tip of the bud equal to ¼ or more of its length.
*As calyx breaks.*—Color—Near Red-Purple, Group 59 A.
*Sepals.*—Inner surface—With fine, wooly tomentum. Margins—With foliaceous appendages; lined with gland-tipped cilia and hairs.
*As first petal opens.*—Size—Small. Form—Short; globular. Color — Outside — Near Red-Purple, Group 59 B, with very small base of near White, Group 155 A. Inside—Near Red, Group 53 A, with very small base of near White, Group 155 A; some outside petals have a near White, Group 155 A streak in center.
*Opening.*—Opens up well; is not retarded or prevented from opening by hot, wet or dry weather.
Bloom:
*Size (when fully open).*—Small; from 1½ inches to 2 inches.
*Petalage.*—Very double; from 100 to 125 petals, plus 8 to 10 petaloids; arranged irregularly; usually with few stamens showing.
*Form.*—Globular at first, but becoming very flat; petals at first being flat, but later becoming tightly imbricated at maturity.
Petals:
*Texture.*—Medium thickness; moderately soft.
*Appearance.*—Inside—Slightly velvety. Outside—Slightly shiny.
*Shape.*—Outside—Nearly oval, with apex rounded. Intermediate—Nearly oval, with apex rounded. Inside—Nearly oval, with apex rounded.

This description of a newly opened flower was made from a rose grown outdoors during the month of May at Hemet, Calif.:

*Color.—Outer petal*—Outside surface—Near Red-Purple, Group 60 A, with very small base of near White, Group 155 A. Inside surface—Near Red, Group 53 A, with very small base of near White, Group 155 A and with some outer petals having near White, Group 155 A in center. *Intermediate petal*—Outside surface—Near Red-Purple, Group 60 A, with very small base, near White, Group 155 A. Inside surface—Near Red, Group 53 A, with very small base of near White Group 155 A. *Inner petal*—Outside surface—Near Red-Purple, Group 59 A, with very small base of near White, Group 155 A. Inside surface—Near Red, Group 53 A, with very small base of near White, Group 155 A.

This description was made from a rose that was open for three days outdoors during the month of May at Hemet, Calif.:

*Color.—Outer petal*—Outside surface—Near Red-Purple, Group 60 A, with small base of near White, Group 155 A. Inside surface—Near Red, Group 53 A, with small base of near White, Group 155 A. *Inner petal*—Outside surface—Near Red-Purple, Group 60 B, with base of near White, Group 155 A. Inside surface—Near Red, Group 53 A, with base of near White, Group 155 A.
*General color effect.*—Newly opened flower—Velvety red. 3-days open—Velvety red, with some bluing of terminal flowers.
*Behaviour.*—Drop off cleanly
*Flower longevity.*—On bush in garden—4 or 5 days in May. Cut roses grown outdoors and kept at living-room temperatures—4 or 5 days in May. Cut roses grown in greenhouse and kept at living-room temperatures—4 or 5 days in May.

*Reproductive organs*

Stamens: Few; arranged regularly about pistils.
Filaments: Short; few with anthers.
Anthers: Small; all open approximately at once.
*Color.*—Upper side—Near Yellow-Orange, Group 19 A. Under side—Near Yellow-Orange, Group 22 B.
Pollen: Very sparse.
Pistils: Few (approximately 40).
Styles: Moderately even; average length; thin; somewhat bunched.
Stigma:
*Color.*—Near Yellow-Green, Group 153 D.
Ovaries: Usually most enclosed in calyx.
Hips: None observed.
Sepals: Falling soon; medium length; almost straight down.
*Color.*—Inside—Near Green, Group 148 C. Outside—Near Greyed-Red, Group 178 A, with near Yellow-Green, Group 144 A at the base.
Seeds: None observed.

*Plant*

Foliage:
*Leaves.*—Compound of usually 5–7 leaflets; normal abundance; medium size; moderately heavy; somewhat leathery and semi-glossy.
*Leaflets.* — Shape — Oblong. Apex — Mucronate. Base—Nearly round. Margin—Serrate.
*Color.*—Mature—Upper surface—Near Yellow-Green, Group 147 A. Under surface—Near Yellow-Green, Group 147 B. Young—Upper surface—Near Yellow-Green, Group 146 A. Under surface—Near Yellow-Green, Group 146 B.
*Rachis (the supporting stem of the compound leaf).*— Average size. Upper side—Grooved; some stipitate glands on edges. Under side—Moderately prickly; with stipitate glands.
*Stipules.*—Long; medium width; with medium length points turning out at an angle of less than 45°.

*Disease resistance.*—Mildly subject to mildew, as determined by comparison with other rose varieties grown under comparable conditions at Hemet, Calif.
Growth:
*Habit.*—Short; bushy; much-branched.
*Growth.*—Moderately vigorous.
*Canes.*—Medium caliper.
*Main stems.*—Color—Near Yellow-Green, Group 148 A. *Large prickles*—Several; medium length; almost straight; with medium length, narrow base. Color—Near Greyed-Orange, Group 165 A. *Small prickles* — Few. *Color* — Near Greyed-Orange, Group 165 A. *Hairs*—None.
*Branches.*—Color—Near Yellow-Green; Group 146 B. *Large prickles*—Several; medium length; almost straight; with medium length, narrow base. Color—Near Greyed-Orange, Group 165 A. *Small prickles*—Few. Color—Near Greyed-Orange, Group 166 A. *Hairs*—None.
*New Shoots.*—Color—Near Greyed-Purple, Group 187 A, with shades of near Yellow-Green, Group 146 B. *Large prickles*—Few; medium length; almost straight; with medium length, narrow base. Color—Near Greyed-Purple, Group 187 C. *Small prickles*—Few. *Hairs*—None.

I claim:

1. A new and distinct variety of rose plant of the floribunda class, substantially as herein shown and described, characterized particularly as to novelty by the unique combination of a low-growing and vigorous plant habit, excellent foliage, a free flowering habit, dainty "Garnette"-like buds which open to small, flat, perfectly formed, attractive full flowers of over 100 petals per flower on the average, a distinctive and attractive velvety red flower color, good flower color retention even under adverse weather conditions, and an above average lasting quality of the flowers both on the bush and as cut flowers.

No references cited.

ROBERT E. BAGWILL, Primary Examiner